United States Patent [19]
Honbo et al.

[11] Patent Number: 5,215,995
[45] Date of Patent: Jun. 1, 1993

[54] HAIR REVITALIZING AGENT

[75] Inventors: Toshiyasu Honbo, Kobe; Takehisa Hata, Nagaokakyo; Akihiro Ishino; Yoshiharu Tsuji, both of Yokohama, all of Japan

[73] Assignee: Fujisawa Pharmaceutical Co., Ltd., Osaka, Japan

[21] Appl. No.: 863,490

[22] Filed: Apr. 2, 1992

Related U.S. Application Data

[63] Continuation of Ser. No. 595,842, Oct. 11, 1990, abandoned.

[30] Foreign Application Priority Data

Oct. 16, 1989 [JP] Japan .................................. 1-266106

[51] Int. Cl.$^5$ ........................................... A61K 31/44
[52] U.S. Cl. .................................. 514/291; 514/450
[58] Field of Search ........................... 514/291, 450

[56] References Cited

U.S. PATENT DOCUMENTS

| | | | |
|---|---|---|---|
| 4,874,791 | 10/1989 | Adachi et al. | 514/558 |
| 4,894,366 | 1/1990 | Okuhara et al. | 514/291 |
| 4,929,611 | 5/1990 | Okuhara et al. | 514/291 |
| 4,956,352 | 9/1990 | Okuhara et al. | 514/291 |
| 5,015,470 | 5/1991 | Gibxon | 424/70 |
| 5,025,026 | 6/1991 | Osamu | 514/356 |
| 5,037,643 | 8/1991 | Green | 424/70 |
| 5,043,162 | 8/1991 | Trager | 424/401 |
| 5,055,456 | 10/1991 | Harris et al. | 514/57 |

FOREIGN PATENT DOCUMENTS

| | | |
|---|---|---|
| 0315978 | 5/1989 | European Pat. Off. |
| 0323042 | 7/1989 | European Pat. Off. |
| 0356399 | 2/1990 | European Pat. Off. |

OTHER PUBLICATIONS

The New York Times, "New Drug Shows Stunning Success in Organ-Transplant Operations", Oct. 18, 1989, pp. A1 and B7.

De Villez, Journal of the American Academy of Dermatology 1989, vol. 16, pp. 669-672 *Androgenetic Alopecia Treated With Topical Minoxidil.*

PDR 45 Ed. 1991, Physicians' Desk Reference, Product Information *Rogaine* pp. 2252-2255.

Transplantation Proceedings, vol. XX, No. 3, Suppl 4 (Jun.), 1988 pp. 109-111, "Effects of Oral and Topical Cyclosporine in Male Pattern Alopecia", D. D. Picascia and H. H. Roenigk, Jr.

Oba, Fragrance Journal No. 80, 109-114, 1986, Japanese with partial translation.

Hattori et al, The Journal of Dermatology, vol. 10, pp. 45-54, 1983.

Adachi et al, Fragrance Journal, 1989-5, pp. 73-79, with partial translation.

*Primary Examiner*—Frederick E. Waddell
*Assistant Examiner*—F. Tsung
*Attorney, Agent, or Firm*—Oblon, Spivak, McClelland, Maier & Neustadt

[57] ABSTRACT

A hair revitalizing agent including a compound represented by the formula shown below or a pharmaceutically acceptable salt thereof:

(wherein $R^1$ to $R^{10}$, $R^{14}$ to $R^{23}$, X, Y, and n are the same as defined in the present specification).

3 Claims, No Drawings

HAIR REVITALIZING AGENT

This application is a continuation of application Ser. No. 07/595,842, filed on Oct. 11, 1990, now abandoned.

BACKGROUND OF THE INVENTION

1. Field of the Invention

This invention relates to a novel hair revitalizing agent. More particularly, it relates the use as a hair revitalizing agent of a tricyclo compound represented by the formula (I) shown below, or a pharmaceutically acceptable salt thereof:

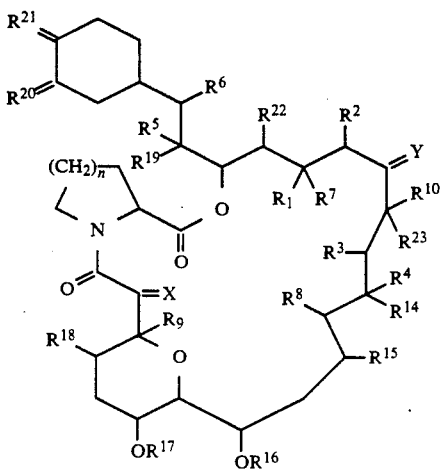

In the above formula, each adjoining pair of $R^1$ and $R^2$, $R^3$ and $R^4$, $R^5$ and $R^6$ independently, a) represents two adjoining hydrogen atoms, or b) forms another bond with a carbon atom to which it is bonded, and in addition thereto, $R^2$ may be an alkyl group;

$R^7$ represents a hydrogen atom, a hydroxy group, a protected hydroxy group, or an alkyloxy group, or an oxo group together with $R^1$;

$R^8$ and $R^9$ independently represent a hydrogen atom or hydroxy group;

$R^{10}$ represents a hydrogen atom, an alkyl group, an alkyl group substituted with 1 or more hydroxy group, an alkenyl group, an alkenyl group substituted with 1 or more hydroxy group, or an alkyl group substituted with an oxo group;

X represents an oxo group, (hydrogen atom, hydroxy group), (hydrogen atom, hydrogen atom) or a group represented by $-CH_2O-$;

Y represents an oxo group, (hydrogen atom, hydroxy group), (hydrogen atom, hydrogen atom), or a group represented by the formula $N-NR^{11}R^{12}$ or $N-OR^{13}$;

$R^{11}$ and $R^{12}$ independently represent a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ independently represent a hydrogen atom or an alkyl group;

$R^{20}$ and $R^{21}$ independently represent an oxo group, or each independently ($R_a^{20}$, hydrogen atom) and $R_a^{21}$, hydrogen atom), $R_a^{20}$ and $R_a^{21}$ independently represent an hydroxy group, an alkyloxy group or a group represented by the formula $OCH_2OCH_2CH_2OCH_3$, or $R_a^{21}$ represents a protected a hydroxy group, and further, $R_a^{20}$ and $R_a^{21}$ taken together form an oxygen atom in an epoxy ring, and n represents 1, 2 or 3.

In addition to the above, Y and $R^{10}$ and $R^{23}$, together with the carbon atoms to which they are bonded, represent a heterocyclic group containing a nitrogen atom, sulfur atom or oxygen atom comprising a saturated or unsaturated 5- or 6-membered ring, and the heterocyclic group may be substituted with one or more group selected from an alkyl group, a hydroxy group, an alkyl group substituted with one or more hydroxy groups, an alkyloxy group, a benzyl group, and a group represented by $-CH_2Se(C_6H_5)$.

2. Description of the Related Art

The tricyclo compound (I) and a pharmaceutically acceptable salt thereof to be used in the present invention are known to have pharmacological effects such as an excellent immunosuppressive action and antimicrobial actions, and are useful for the therapy and prophylaxis of a rejection of transplanted organs or tissues, graft-versus- host diseases reactions to grafting, various autoimmune diseases, and infectious diseases (Japanese Unexamined Patent Publication (Kokai) No. 61-148181).

Baldness or alopecia, in addition to (1) male pattern alopecia and (2) alopecia senilis, includes (3) alopecia areata, and further, diseases accompanied by basic skin lesions such as (4) cicatrix or (5) infectious tumors, or (6) accompanied by systemic disorders, for example, an internal secretion abnormality or nutritional disorder.

Among the above, (3) to (6) can all heal naturally or can be healed by curing the causes thereof.

Also, concerning (3) alopecia areata, it is considered that a autoimmune phenomenon participates therein, and therefore, the administration of a substance having an immunosuppressive action has been attempted. Accordingly, the tricyclo compound (I), which has a potent immunosuppressive action, obviously can have therapeutical effect on alopecia areata.

On the other hand, the causes of (1) male pattern alopecia and (2) alopecia senilis are considered to be (1) an activation of male hormones at organs such as hair roots and the sebum gland, (2) a lowering in the amount of blood reaching the hair follicles (3) a scalp abnormality caused by an excessive secretion of sebum, a formation of peroxides, or a propagation of bacteria, (4) genetic causes, and (5) aging.

For such reasons, hair revitalizing materials of the prior art generally comprise compounds having the actions of removing or alleviating the causes mentioned above formulated therein. For example, a compound having the action of inhibiting the activation of male hormones, or a compound having the action of increasing the amount of blood reaching the hair follicles, is formulated.

Nevertheless, in male pattern alopecia and alopecia senilis, the epilation mechanism and the hair generation mechanism are very complicated, and by merely inhibiting an activation of male hormones or increasing the amount of blood reaching the hair follicles, as practiced in the prior art, does not sufficiently treat or prevent baldness or alopecia. Accordingly, there has long been demanded the development of a hair revitalizing agent for male pattern alopecia and alopecia senilis, by which a satisfactory effect is exhibited. Therefore, the present inventors made an intensively study of this problem, and consequently, unexpectedly found that the tricyclo compound (I) has an excellent hair revitalizing effect for male pattern alopecia and alopecia senilis, to thereby accomplish the present invention.

SUMMARY OF THE INVENTION

According to the present invention, there is provided a new use of a substance which has been newly found to have an excellent hair revitalizing effect. More specifically, the present invention provides a new use of a compound represented by the formula (I) shown below or a pharmaceutically acceptable salt thereof:

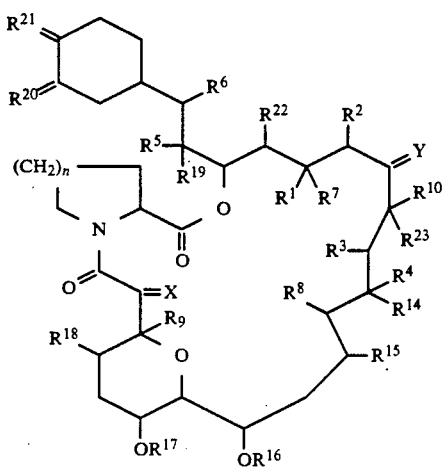

Wherein, $R^1$ to $R^{10}$, $R^{14}$ to $R^{23}$, X, Y and n are as defined above, which can be used as a hair revitalizing agent.

In particular, there is provided a hair revitalizing agent including the compound of the above formula (I), which can be used to combat male pattern alopecia or alopecia senilis.

DESCRIPTION OF THE PREFERRED EMBODIMENTS

The present invention is now described in detail.

In the present specification, "lower" means a group having 1 to 6 carbon atoms, unless otherwise specified.

Preferable examples of an alkyl group include straight or branched aliphatic hydrocarbon residues, for example, lower alkyl groups such as methyl, ethyl, propyl, isopropyl, butyl, isobutyl, pentyl, neopentyl, hexyl, and the like.

Preferable examples of the alkenyl group include straight or branched aliphatic hydrocarbon residues containing one double bond, for example, lower alkenyl groups such as vinyl, propenyl, butenyl, methylpropenyl, pentenyl, hexenyl, and the like.

Preferable examples of the aryl group include phenyl, tolyl, xylyl, cumenyl, mesityl, and naphthyl.

As suitable protective groups in the protected hydroxy group, there are included, for example, 1-(lower alkylthio) (lower) alkyl groups such as methylthiomethyl, ethylthiomethyl, propylthiomethyl, isopropylthiomethyl, butylthiomethyl, isobutylthiomethyl, hexylthiomethyl and the like, more preferably $C_1$-$C_4$ alkylthiomethyl group, most preferably methiothiomethyl group; tri-substituted silyl groups, for example, tri-(lower)alkylsilyl such as trimethylsilyl, triethylsilyl, tributylsilyl, tert-butyl-dimethylsilyl, tri-tert-butylsilyl and the like, lower alkyldiarylsilyl such as methyldiphenylsilyl, ethyldiphenylsilyl, propyl-diphenylsilyl, tert-butyldiphenylsilyl and the like, more preferably tri($C_1$-$C_4$) alkylsilyl group and $C_1$-$C_4$ alkyl-diphenylsilyl group, most preferably tert-butyl-dimethyl silyl group and tert-butyl-diphenylsilyl group; acyl groups such as aliphatic acyl groups, aromatic acyl groups derived from carboxylic acids, sulfonic acids and carbamic acids and aliphatic acyl groups substituted with aromatic groups; and so on.

Examples of aliphatic acyl groups include lower alkanoyl groups which may have one or more suitable substituent such as carboxy (e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl), cyclo(lower)alkoxy(lower)alkanoyl groups which may have one or more suitable substituent such as lower alkyl (e.g., cyclopropyloxyacetyl, cyclobutyloxypropionyl, cycloheptyloxybutyryl, menthyloxyacetyl, menthyloxypropionyl, menthyloxybutyryl, methyloxypentanoyl, menthyloxyhexanoyl), camphorsulfonyl group; lower alkylcarbamoyl groups having one or more suitable substituent such as carboxy or protected carboxy group, as exemplified by carboxy(lower)-alkylcarbamoyl groups (e.g., carboxymethylcarbamoyl, carboxyethylcarbamoyl, carboxypropylcarbamoyl, carboxybutylcarbamoyl, carboxypenthylcarbamoyl, carboxyhexylcarbamoyl) or protected carboxy(lower)alkylcarbamoyl groups such as tri(lower)alkylsilyl(lower)alkoxycarbonyl(lower)alkylcarbamoyl groups (e.g., trimethylsilylmethoxycarbonylethylcarbamoyl, trimethylsilylethoxycarbonylpropylcarbamoyl, triethylsilylethoxycarbonylpropylcarbamoyl, t-butyldimethylsilylethoxycarbonylpropylcarbamoyl, trimethylsilylpropoxycarboylbutylcarbamoyl), and so on.

Examples of the aromatic acyl group include aroyl groups which may have one or more suitable substituent such as nitro (e.g., benzoyl, toluoyl, xyloyl, naphthoyl, nitrobenzoyl, dinitrobenzoyl, nitronaphthoyl and the like), and arenesulfonyl groups which may have one or more suitable substituent such as halogen (e.g., benzenesulfonyl, toluenesulfonyl, xylenesulfonyl, naphthalene-sulfonyl, fluorobenzenesulfonyl, chlorobenzensulfonyl, bromo-benzenesulfonyl, iodobenzenesulfonyl).

Examples of the aliphatic acyl group substituted with aromatic group include ar(lower) alkanoyl groups which may have one or more suitable substituent such as lower alkoxy and trihalo(lower)alkyl (e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl).

Among the above-mentioned acyl groups, further preferable acyl groups are $C_1$-$C_4$ alkanoyl groups which may have carboxy, cyclo($C_5$-$C_6$)alkyloxy($C_1$-$C_4$) alkanoyl groups having 2 ($C_1$-$C_4$)alkyls at the cycloalkyl moiety, camphorsulfonyl group, carboxy($C_1$-$C_4$) alkylcarbamoyl groups, tri($C_1$-$C_4$)alkylsilyl($C_1$-$C_4$) alkoxycarbonyl($C_1$-$C_4$)alkylcarbamoyl groups, benzoyl groups which may have 1 or 2 nitro group, benzensulfonyl groups having halogen, phenyl($C_1$-$C_4$) alkanoyl groups having $C_1$-$C_4$ alkoxy and trihalo($C_1$-$C_4$) alkyl, and thereamong, most preferable are acetyl, carboxypropionyl, methyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the heterocyclic group having a nitrogen atom, sulfur atom or oxygen atom comprising a 5- or 6-membered ring include pyrrolyl group, tetrahydrofuryl group, and others.

As the pharmaceutically acceptable salt of the tricyclo compound (I), there are included non-toxic pharmaceutically acceptable salts, namely salts with inorganic or organic bases such as alkali metal salts (e.g., sodium, potassium salts), alkaline earth metal salts (e.g., calcium, magnesium salts), and ammonium salts, amine salts (e.g., triethylamine, N-benzyl-N-methylamine salts).

In the tricyclo compound (I), there may exist a pair or more of steric isomers such as conformers, optical isomers and geometrical isomers, due to an asymmetric carbon atom and double bond, and such conformers or isomers are also included within the scope of the present invention.

Among the tricyclo compounds (I) to be used in the present invention, the compound represented by the following structural formula is the most preferred.

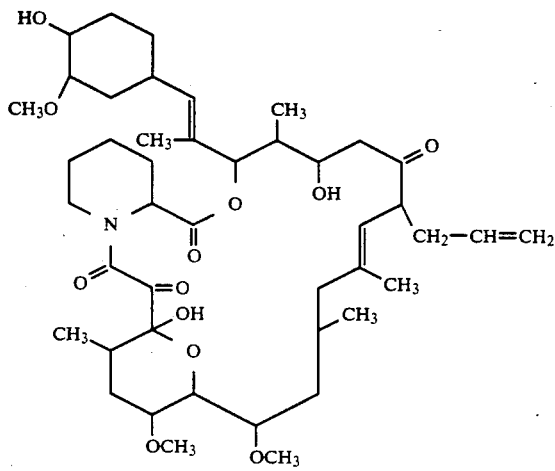

(hereinafter called FK-506). The compound is named 17-allyl-1, 14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

The tricyclo compound (I) or a salt thereof can be obtained by the process described in Japanese Unexamined Patent Publication (Kokai) No. 61-148181. Particularly, FK-506 can be produced by fermentation of Streptomyces tsukubaensis No. 999 (FERM BP-927).

In the present specification, the term hair revitalizing effect or hair revitalizing action means epilation prevention, hair germination, and a promotion of hair generation and hair growth.

Preparation formation

Next, the preparation of the tricyclo compound (I) for application as a hair revitalizing material is described.

The hair revitalizing material of the present invention is used in the form of a mixture in which, in addition to the tricyclo compound (I), acceptable additives and other drugs conventionally used as hair revitalizing materials are added. Examples of these additives and drugs include antibacterial agents such as hinokitiol, hexachlorophen, phenol, benzalkonium chloride, cetylpyridinium chloride, undecylenic acid, trichlorocarbanilide and bithionol, antiphologistic agents or refrigerants such as glycyrrhizinic acid and derivatives thereof (e.g., ammonium salt), allantoin, mentol, etc., skin activators such as pantothenic acid and derivatives thereof, pantothenol and derivatives thereof, saponin, etc., circulation promoters such as Swelchnogen, vitamin E nicotinic acid ester, cefratin etc., skin peripheral vasodilators such as capronium chloride, vitamine B6 hydrochloride, acetylcholin derivatives, etc., keratolytic agents such as salicyclic acid, resorcin, etc., drugs such as zinc and compounds thereof, etc., galenical extracts such as of capsicum tincture, licorice, lithospermum root, runner, ginseng, etc., animal and vegetable oils such as olive oil, macadamia nut, squalane, etc., hydrocarbon oils as represented by fluid paraffin, ester oils such as isopropyl myristate, 2-ethylhexylpalmitate, etc., waxes such as beeswax, carunauba wax, etc., oils such as higher fatty acids, higher alcohols, etc., lactic acid and derivatives thereof such as alkyl ester, etc., polyhydric alcohols such as polyethylene glycol, glycerine, sorbitol, etc., humectants such as mucopolysaccharides, pyrrolidone carboxylic acid salts, etc., thickeners such as hydroxypropylmethyl cellulose, carboxyvinyl polymer, gelatin, gum arabic, polyvinyl alcohol, etc., lower alcohols such as ethanol, etc., water, vitamins, hormones, amino acids, surfactants, solubilizing agents, antioxidants, UV-ray absorbers, perfumes, and dyes, etc., and these may be used alone or as a mixture of two or more thereof.

The dosage form of the hair revitalizing agent of the present invention can be any desired form, provided that it can be externally applied. For example, external drug creams, such as lotions, liniments, milky lotions, etc., external semi-solid preparations such as ointments, pasta, jelly, sprays, etc., and hair shampoos and hair rinses can be included.

In the hair revitalizing agent of the present invention, the amount formulated of the tricyclo compound (I), which is the active ingredient, is not particularly limited, but may be formulated within the range of, for example, from 0.0001 to 60% by weight (hereinafter % represents % by weight), preferably from 0.001 to 10%, most preferably from 0.005 to 0.8%.

Administration form

The hair revitalizing agent of the present invention is administered method by a percutaneous administration or by spraying onto the skin. The dose of the hair revitalizing agent of the present invention varies depending on the age, individual differences, and the condition of the disease, and cannot be clearly defined, but in general, the percutaneous dose of the tricyclo compound (I) for a human being is preferably 0.00001 to 1000 mg, more preferably 0.0001 to 500 mg, per day. The above-mentioned dose can be administered once or in 2 to 4 divided portions per day.

Hair revitalizing test example (1) Hair generation test with mouse I

To determine the hair revitalizing effect of the present invention, a hair generation test using a mouse was conducted. The back of a C3H/HeNCrj male mouse at the resting stage was depilated by a razor, and the three kinds of samples shown in Table 1 were each coated thereon in an amount of 0.12 ml, once per day, and the conversion from the resting stage to the growing stage was observed.

In the groups to which the test drugs of Samples 1 and 2 were administered, a complete conversion from the resting stage to the growing stage was observed over the whole region of the depilated portion, with all of the examples, after an elapse of about 1 week, whereby a hair generation was rapidly commenced. In the group administered with Sample 3 used as Control, after the elapse of about one week, only a conversion to the growing stage was observed locally at the depilated portion, in only one example, with the remainder all at the resisting stage.

TABLE 1

| Group | Composition of test solution |
|---|---|
| 1 | 50% ethanolic solution containing 0.1% FK-506 |
| 2 | 50% ethanolic solution containing 1% FK-506 |
| 3 (Control) | 50% ethanol |

(2) Hair generation test with mouse II

The back of a C3H/HeNCrj strain male mouse at the resting stage was depilated by a razor, and three kinds of samples shown in Table 2 were each coated thereon in an amount of 0.1 ml, once per day. The effect was judged from the hair generation area ratio, calculated on the basis of photographs.

TABLE 2

| Group | Composition of test solution |
|---|---|
| 4 | 70% ethanolic solution containing 0.1% FK-506 |
| 5 | 70% ethanolic solution containing 1% α-tocopherol acetate |
| 6 (Control) | 70% ethanol |

Results

Table 3 shows the hair generation area ratio and determination 2 weeks after the coating.

TABLE 3

| Sample | Hair generation area ratio (%)* | Determination |
|---|---|---|
| 4 | 75.3 ± 8.5 | Very strong effect |
| 5 | 5.9 ± 3.2 | Weak effect |
| 6 | 0.0 ± 0.0 | No effect |

*Mean ± S.E.

As apparent from the above results, the tricyclo compound (I) has a remarkable effect as a hair revitalizing agent, and thus the hair revitalizing agent of the present invention has an excellent effect.

EXAMPLES

Referring now to Examples, the preparation method of the hair revitalizing agent according to the present invention is described in detail. In the Examples, % indicates % by weight.

Example 1

A lotion comprising the composition shown below was prepared.

| | (%) |
|---|---|
| 95% Ethanol | 80.0 |
| FK-506 | 10.0 |
| α-Tocopherol acetate | 0.01 |
| Ethylene oxide (40 mole) adducts of hardened castor oil | 0.5 |
| Purified water | 9.0 |

-continued

| | (%) |
|---|---|
| perfume and dye | q.s. |

Into 95% ethanol were added FK-506, α-tocopherol acetate, ethylene oxide (40 mole) adducts of hardened castor oil, perfume, and a dye, and the mixture was stirred and dissolved, followed by an addition of purified water, to obtain a transparent liquid lotion.

The lotion was coated once or twice per day, in an amount of 5 ml each time, at a site having marked baldness or alopecia.

Example 2

A lotion comprising the composition shown below was prepared.

| | (%) |
|---|---|
| 95% Ethanol | 80.0 |
| FK-506 | 0.005 |
| Hinokitiol | 0.01 |
| Ethylene oxide (40 mole) adducts of hardened castor oil | 0.5 |
| Purified water | 19.0 |
| Perfume and dye | q.s. |

Into 95% ethanol were added FK-506, hinokitiol, ethylene oxide (40 mole) adducts of hardened castor oil, perfume, and a dye, and the mixture was stirred and dissolved, followed by an addition of purified water, to obtain a transparent liquid lotion.

The lotion was coated by spraying once to 4 times per day.

Example 3

An emulsion was prepared from A phase and B phase having the following compositions.

| | (%) |
|---|---|
| (A phase) | |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitane monooleate | 1.0 |
| FK-506 | 0.01 |
| (B phase) | |
| Glycerine | 10.0 |
| Purified water | 69.0 |
| Perfume, dye, and preservative | q.s. |

The A phase and the B phase were respectively heated and melted and maintained at 80° C., both phases were mixed to be emulsified, and were cooled under stirring to normal temperature to obtain an emulsion. The emulsion was coated by spraying once to four times per day.

Example 4

A cream was prepared from A phase and B phase having the following compositions.

| | (%) |
|---|---|
| (A phase) | |
| Fluid paraffin | 5.0 |

| | (%) |
|---|---|
| Cetostearyl alcohol | 5.5 |
| Petrolatum | 5.5 |
| Glycerine monostearate | 3.0 |
| Polyoxyethylene (20 mole) 2-octyldodecyl ether | 3.0 |
| Propylparaben | 0.3 |
| (B phase) | |
| FK-506 | 0.8 |
| Glycerine | 7.0 |
| Dipropylene glycol | 20.0 |
| Polyethylene glycol 4000 | 5.0 |
| Sodium hexametaphosphate | 0.005 |
| Purified water | 44.895 |

The A phase is heated and melted, and maintained at 70° C., the B phase was added into the A phase followed by stirring, and the obtained emulsion was cooled to obtain a cream.

The cream was coated on the skin once to 4 times per day.

EXAMPLE 5

A hair liquid comprising the composition shown below was prepared.

| | (%) |
|---|---|
| Polyoxyethylene butyl ether | 20.0 |
| Ethanol | 50.0 |
| FK-506 | 0.001 |
| Propylene glycol | 5.0 |
| Polyoxyethylene hardened castol oil | 0.4 |
| Perfume | q.s. |
| Purified water | q.s. |

Into ethanol were added polyoxypropylene butyl ether, propylene glycol, polyoxyethylene hardened castor oil, FK-506, and perfume, which were mixed under stirring, and to the mixture was added purified water, to obtain a hair liquid.

Example 6

A hair shampoo comprising the composition shown below was prepared.

| | (%) |
|---|---|
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| FK-506 | 5.0 |
| Ethanol | 2.0 |
| Perfume | 0.3 |
| Purified water | 69.7 |

Into 69.7 g of purified water were added 5.0 g of sodium laurylsulfate, 5.0 g of triethanolamine laurylsulfate, 6.0 g of betaine lauryldimethylaminoacetate, then a mixture obtained by adding 5.0 g of FK-506, 5.0 g of polyethylene glycol, and 2.0 g of ethylene glycol distearate to 2.0 g of ethanol, followed by stirring, and 0.3 g of perfume, were successively added, and the mixture was heated then cooled to obtain a hair shampoo. The hair shampoo was used on the scalp once or twice per day.

We claim:

1. A method of treating male pattern alopecia in a patient requiring hair generation stimulating treatment, which comprises applying to the skin area of the patient where such alopecia occurs, an effective hair generation stimulating amount of a compound of the formula shown below, or a pharmaceutically acceptable salt thereof:

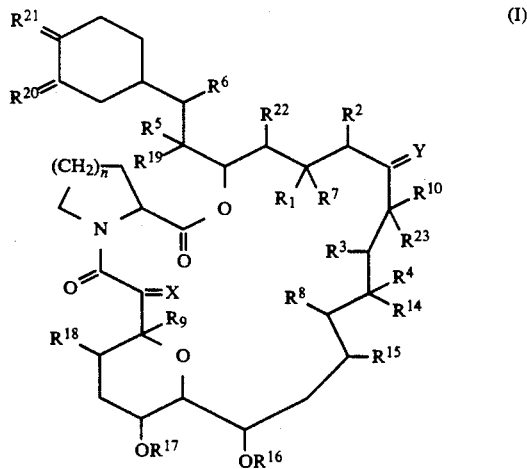

wherein each adjoining pair of $R^1$ and $R^2$, $R^3$ and $R^4$, $R^5$ and $R^6$ independently, a) represents two adjoining hydrogen atoms, or b) forms another bond with a carbon atom to which it is bonded, and in addition thereto, $R^2$ may be an alkyl group;

$R^7$ represents a hydrogen atom, a hydroxy group, a protected hydroxy group, or an alkyloxy group, or represents an oxo group together with $R^1$;

$R^8$ and $R^9$ independently represent a hydrogen atom, or a hydroxy group;

$R^{10}$ represents a hydrogen atom, an alkyl group, an alkyl group substituted with 1 or, more hydroxy groups, an alkenyl group, an alkenyl group substituted with 1 or more hydroxy groups, or an alkyl group substituted with an oxo group;

X represents an oxo group, (hydrogen atom, hydroxy group), hydrogen atom, hydrogen atom) or a group represented by $-CH_2O-$;

Y represents an oxo group, (hydrogen atom, hydroxy group), (hydrogen atom, hydrogen atom), or a group represented by the formula $N-NR^{11}R^{12}$ or $N-OR^{13}$;

$R^{11}$ and $R^{12}$ independently represent a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$, $R^{23}$ independently represent a hydrogen atom or an alkyl group;

$R^{20}$ and $R^{21}$ independently represent an oxo group, or may be each independently ($R_a^{20}$, hydrogen atom) and $R_1^{21}$, hydrogen atom); $R_a^{20}$ and $R_a^{21}$ independently represent a hydroxy group, an alkyloxy group or a group represented by the formula $OCH_2OCH_2CH_2OCH_3$, or $R_a^{21}$ represents a protected hydroxy group, and further, $R_1^{20}$ and $R_a^{21}$ taken together form an oxygen atom in an epoxy ring;

n represents 1, 2 or 3, and in addition to the above meanings, Y, $R^{10}$, and $R^{23}$ together with the carbon atoms to which they are bonded may represent a heterocyclic group containing nitrogen atom, sulfur atom or oxygen atom comprising a saturated or unsaturated 5- or 6-membered ring, and the heterocyclic group may be substituted with 1 or more group selected from alkyl groups, hydroxy group, alkyl groups substituted with 1 or more hydroxy group, alkyloxy groups, benzyl group and the group represented by —CH$_2$Se (C$_6$H$_5$).

2. A method of treating male pattern alopecia in a patient requiring hair generation stimulating treatment, which comprises applying to the skin area of the patient where such alopecia occurs, an effective hair generation stimulating amount of a compound of the formula shown below, or a pharmaceutically acceptable salt thereof;

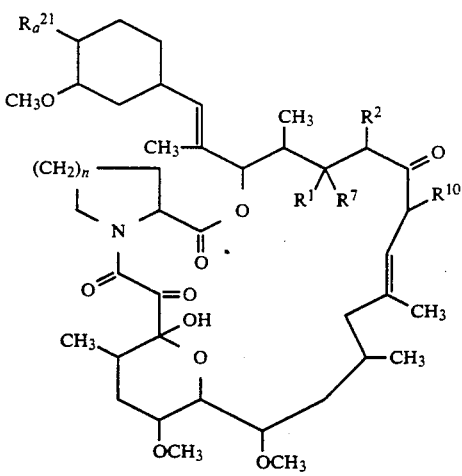

wherein adjoining pair of R$^1$ and R$^2$,
a) represents two adjoining hydrogen atoms, or
b) forms another bond with a carbon atom to which it is bonded;
R$^7$ represents a hydrogen atom or the same meanings as R$_a^{21}$ defined below;
R$^{10}$ represents methyl, ethyl, propyl, or allyl;
R$_a^{21}$ represents hydroxy or pharmaceutically acceptable protected hydroxy selected from 1-(lower alkylthio) (lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy; and is an integer 1 or 2.

3. A method according to claim 1 in which the compound is 17-allyl-1, 14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

* * * * *